(12) United States Patent
Wu et al.

(10) Patent No.: US 8,063,361 B2
(45) Date of Patent: Nov. 22, 2011

(54) ION MOBILITY BASED SEPARATION METHODS AND APPARATUS

(75) Inventors: Ching Wu, Acton, MA (US); Clinton Alawn Krueger, Milton, MA (US)

(73) Assignee: Excellims Corporation, Acton, MA (US)

( * ) Notice: Subject to any disclaimer, the term of this patent is extended or adjusted under 35 U.S.C. 154(b) by 192 days.

(21) Appl. No.: 12/610,306

(22) Filed: Oct. 31, 2009

(65) Prior Publication Data

US 2010/0108877 A1 May 6, 2010

Related U.S. Application Data

(63) Continuation-in-part of application No. 12/026,192, filed on Feb. 5, 2008, now Pat. No. 7,696,474.

(60) Provisional application No. 61/109,946, filed on Oct. 31, 2008.

(51) Int. Cl.
*H01J 49/00* (2006.01)
*H01J 49/26* (2006.01)
*B01D 59/44* (2006.01)

(52) U.S. Cl. ......... 250/288; 250/281; 250/282; 250/287

(58) Field of Classification Search .................. 250/281, 250/282, 288, 287
See application file for complete search history.

(56) References Cited

U.S. PATENT DOCUMENTS

| | | | |
|---|---|---|---|
| 5,338,931 A * | 8/1994 | Spangler et al. | 250/287 |
| 6,107,628 A | 8/2000 | Smith | |
| 6,481,263 B1 | 11/2002 | Haley | |
| 6,690,004 B2 | 2/2004 | Miller | |
| 6,727,495 B2 | 4/2004 | Li | |
| 7,385,210 B2 * | 6/2008 | Ulrich et al. | 250/492.3 |
| 2003/0209665 A1 | 11/2003 | Losch | |
| 2004/0178340 A1 | 9/2004 | Karas | |
| 2005/0109930 A1 | 5/2005 | Hill | |
| 2005/0156107 A1 | 7/2005 | Miller | |
| 2005/0178964 A1 | 8/2005 | Guevremont | |
| 2005/0205775 A1 | 9/2005 | Bromberg | |
| 2006/0192102 A1 | 8/2006 | Miller | |
| 2006/0289747 A1 | 12/2006 | Schultz | |
| 2007/0084999 A1 | 4/2007 | Miller | |
| 2008/0169417 A1 | 7/2008 | Cohn | |
| 2008/0210861 A1 | 9/2008 | Wu | |
| 2010/0127166 A1 * | 5/2010 | Krueger et al. | 250/282 |
| 2010/0148058 A1 * | 6/2010 | Krueger et al. | 250/282 |

FOREIGN PATENT DOCUMENTS

WO WO2006114580 A1 11/2006

* cited by examiner

*Primary Examiner* — Nikita Wells

(57) ABSTRACT

The present invention describes separating components in a sample in an ion mobility based spectrometer using at least one matching property of the components other than the molecular properties in conventional ion mobility measurements in noble drift gases to enhance separation and resolution of the sample. Separation based on the matching property is realized by altering the drift media of the IMS. Besides altering drift media, energy level of ions and/or drift media are also controlled during the separation process. This invention describes an ion mobility apparatus wherein an energy source is added to the IMS that provides additional energy to the ions and/or drift media and tuning methods that involve selecting drift media and optimizing the energy level in order to achieve optimal performance.

27 Claims, 6 Drawing Sheets

ION MOBILITY BASED SEPARATION METHODS AND APPARATUS

CROSS-REFERENCE TO RELATED APPLICATIONS

The present application is continuation in part of U.S. patent application Ser. No. 12/026,192 and claims the benefit of and priority to corresponding U.S. Provisional Patent Application No. 61/109,946, filed Oct. 31, 2008 respectively, the entire content of the applications are herein incorporated by reference.

BACKGROUND OF THE INVENTION

Ion mobility spectrometers (IMS) have become a common tool for detecting trace amounts of chemical and/or biological molecules. Compared to other spectrometric chemical analysis technologies, e.g., mass spectrometry, IMS is a relatively low resolution technique. The IMS advantages of very high sensitivity, small size, low power consumption, and ambient pressure operation are in some cases completely offset, or at a minimum, reduced by the lack of sufficient resolution to prevent unwanted responses to interfering chemical and/or biological molecules. In a general sense, ion mobility spectrometers are currently used to separate components of a sample by differentiating their ion mobilities and/or ion mobility differences under given electric field conditions. Present invention describes differentiating components in a sample in an IMS using at least one additional property of the components besides their ion mobility and/or ion mobility differences.

The present invention is a broad-based method for the analytical separation of samples in general life science research, drug discovery and clinical applications. The invention can be used to separate chemical mixtures that currently require several chromatography methods such as HPLC, chiral chromatography, and ion chromatography.

The present state of the art ion mobility spectrometers lack the ability to perform a separation based on an additional property of the components to be separated in the sample other than the components ion mobility. The additional property of the substance (components to be separated) can be targeted for each substance and therefore the overall IMS separation can be tuned. It is the purpose of this invention to tune the separation in the IMS by using a substances additional property that affects their measured ion mobility.

SUMMARY OF THE INVENTION

In one aspect of the present invention, under low electric field conditions, the ion mobility is related to reduced mass, collision cross section (size and/or shape), and charge state of the ionized sample components and the components are differentiated from each other by the time it takes the components to travel in the drift media under the influence of an electric field or the flight path in an asymmetric electric field under the influence of an electric filed and/or carrier gas flow. In one embodiment, the present invention describes separating components in a sample in an IMS using at least one matching property of the components other than the measured ion mobility in conventional noble drift gas, i.e. reduced mass, collection cross section (size and/or shape) and charge state of the components, to enhance separation and/or resolution of the sample. Separation based on the matching property is realized by altering drift media, e.g. introducing modifier(s) into the drift media of the IMS; such modifier selectively interacts with one or more component in the sample based on the matching property of the sample components. The matching property of a substance (component of the sample) can be utilized to enhance separation and/or resolution of the sample components may include, but not limited to: charge strength, reactivity, polarity, hydrophobic and/or hydrophilic properties, size-exclusion properties, structure selective affinities (affinity), acidity and/or basicity, pH, phase of matter, electromagnetic radiation, magnetism, biological activity, boiling point, etc.

This invention describes an ion mobility apparatus and methods wherein an energy source is added to the IMS providing additional energy to the ions, neutral molecules and/or drift media. The energy could be tuned to alter the degree of the interaction between the sample components and drift media where the drift media includes a variety of drift gases and/or the modifiers. In one embodiment, the additional energy first removes pre-existing ionized sample component-neutral molecule cluster, subsequentially allowing the sample component in free form to interact with drift media at a selected energy level.

BRIEF DESCRIPTION OF THE DRAWINGS

The foregoing and other aspects, embodiments, and features of the inventions can be more fully understood from the following description in conjunction with the accompanying drawings. In the drawings like reference characters generally refer to like features and structural elements throughout the various figures. The drawings are not necessarily to scale, emphasis instead being placed upon illustrating the principles of the inventions.

DETAILED DESCRIPTION OF VARIOUS EMBODIMENTS

Unless otherwise specified in this document the term "ion mobility based spectrometer" is intended to mean any device that separates ions based on their ion mobilities and/or mobility differences under the same or different physical and/or chemical conditions, the spectrometer may also include detecting the ions after the separation process. Many embodiments herein use the time of flight type IMS as examples; the term ion mobility based spectrometer shall also include many other kinds of spectrometers, such as differential mobility spectrometer (DMS) and field asymmetric ion mobility spectrometer (FAIMS), and other derived and/or combined forms of spectrometers. Unless otherwise specified, the term ion mobility spectrometer or IMS is used interchangeable with the term ion mobility based spectrometer defined above.

As used herein, the term "analytical instrument" generally refers to ion mobility based spectrometer, MS, and any other instruments that have the same or similar functions. Unless otherwise specified in this document the term "mass spectrometer" or MS is intended to mean any device or instrument that measures the mass to charge ratio of a chemical/biological compounds that have been converted to an ion or stores ions with the intention to determine the mass to charge ratio at a later time. Examples of MS include, but are not limited to: an ion trap mass spectrometer (ITMS), a time of flight mass spectrometer (TOFMS), and MS with one or more quadrupole mass filters The phrase "and/or," as used herein in the specification and in the claims, should be understood to mean "either or both" of the elements so conjoined, i.e., elements that are conjunctively present in some cases and disjunctively present in other cases.

Unless otherwise specified in this document the term "chemical and/or biological molecule" is intended to mean single or plurality of particles that are, either charged or not charge, derived from atoms, molecules, particles, and subatomic particles.

Figure 1:
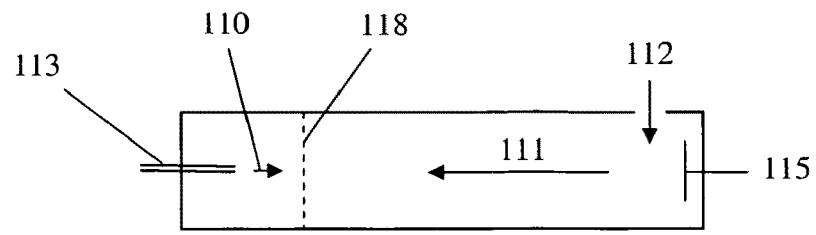
FIG. 1 shows the basic components of a time of flight type IMS system.

The components of a basic time of flight type IMS system are shown in the simple diagram in FIG. 1. Samples are ionized ionization/reaction region (the reaction region is not clearly specified in the drawing) and then are pulsed into the drift region and travel under the influence of a constant electric field in a direction 110 that is opposite to the drift gas flow 111. Ions travel through the ion mobility drift tube while colliding with neutral drift gas molecules (typically an inert gas such as nitrogen). The drift gas 112 is usually added at the opposite end to where the sample is added 113. The ion mobility is related to the ion-drift gas collision processes at the molecular level, through the molecules: reduced mass, collection cross section (size and/or shape) and charge state of the molecule. Ions are detected on a Faraday plate at the end of the drift tube and the time for each ion traveling from the ion gate 118 to the detector 115 is measured.

In one aspect of the present invention, under low electric field conditions, the ion mobility is related to reduced mass, collision cross section (size and/or shape), and charge state of the components and the components are differentiated from each other by the time it takes the components to travel in the drift media under the influence of an electric field. The drift media generally comprise pure or mixture of gases, such as noble gases, interactive gases, and/or chemical modifiers. The ratio of one or more of these gases is adjusted to achieve the maximum IMS performance. In one aspect, if a liquid phase ion mobility measurements is conducted, the drift media may include pure or mixture of chemicals in liquid form. The chemical modifiers are the chemicals that are added to the other parts of the drift media changing the drift media properties. The modifiers are generally homogenously mixed with other parts of the drift media. In one aspect, the modifiers could also be suspending macro-molecules or nano-particles that entrain with the other parts of drift media. In one embodiment, present invention describes separating components in a sample in an IMS simultaneously using at least one matching property of the components other than their intrinsic ion mobility, i.e. reduced mass, collection cross section (size and/or shape) and type of charge state of the components in noble gases to enhance separation and/or resolution of the sample. In this invention, the matching property shall be interpreted as any properties of the sample components (ions) that can affect ion mobility characteristic (such as, drift time, ion fly path, spatial distribution, etc.) in the IMS in a matching drift media. In one aspect, the sample components involve interaction with drift media that is in additional to the state of the art ion mobility based separation. As a non-limiting example, the basicity of the sample components may influence the drift characteristics when acidic drift media is used. However, the word "matching" shall not be interpreted as "basic-acidic"; in many cases they could be either the same or opposite. In this particular example, basic drift media may also cause drift characteristic changes. Separation based on the matching property can be realized by changing drift media, such as introducing modifier(s) into the drift media of the IMS; such modifier selectively interacts with one or more component in the sample based on the matching property of the sample component. The matching property of a substance (component of the sample) can be utilized to enhance separation and/or resolution of the sample components may include, but not limited to: charge strength, reactivity, polarity, hydrophobic and/or hydrophilic properties, size-exclusion properties, structure selective affinities (affinity), acidity and/or basicity, pH, phase of matter, electromagnetic radiation, magnetism, biological activity, boiling point, etc.

Figure 17:
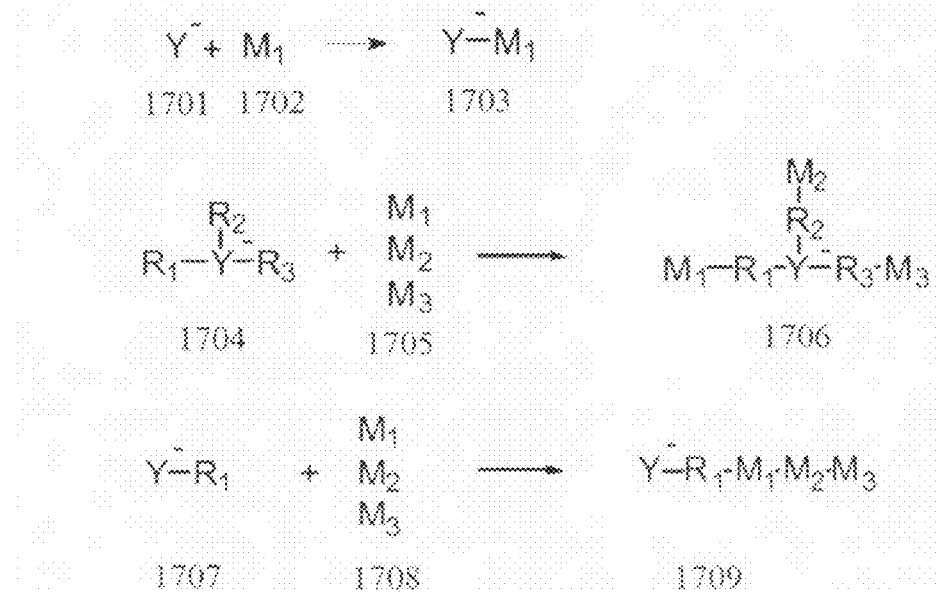
FIG. 17 shows multiple modifier interactions.

As a non-limiting example, for time of flight type IMS when the drift media is changed by adding modifiers, the time it takes the components to travel in the drift media under the influence of an electric field is ether increased or decreased according to the size of the modifiers. The modifiers can be added to the drift gas such that the composition of the drift media is between 0 to 100 percent. The drift gas is normally an inert gas such as nitrogen, so the components travel is retarded by colliding with the nitrogen molecules. Since nitrogen is an inert gas, there is no other interaction force that momentarily keeps the component and the nitrogen molecule together. The component just collides with the nitrogen molecule and is slowed and continues down the drift tube under the influence of the electric field. When a modifier is added along with the nitrogen drift gas a drift media is formed. If the modifier molecule is larger than the nitrogen molecule, the component of the samples travel would be further retarded due to the fact that the collision with this larger modifier would slow the component down more than a collision with the smaller nitrogen molecule. Now, since the modifier may not be a inert gas, interaction forces can further retard the travel of a component of a sample not just the difference in size. If the modifier's interaction force is 100 percent, whereby the modifier binds to the component through the entire travel time, then the time of travel is determined by the increased size of the component, modifier plus component. Therefore, the size of the modifier used to interact with a component of a sample dictates the extended travel time. For the following non-limiting examples a negative ion is discussed, but this method is also valid for positive ions. For example as shown in FIG. 17, if the components 1701 drift time in pure nitrogen as the drift gas is 5 ms and through the addition of modifier 1702 with an similar size and molecular weight as nitrogen, but interacts with modifier 1702 to form molecule 1703 completely, then the drift time may become 9 ms, for instance. In this example the modifier binds to the component through the entire travel time. The difference in drift time of the component between the totally bound modifier 9 ms and no bound modifier 5 ms, is the amount of drift time (4 ms) that the interaction force is 100 percent effective. At 0 effectiveness the difference is 0 ms. Therefore, by tuning the interaction force the additional drift time can be adjusted from 0 to 4 ms in this example. The larger the modifier, the larger the additional drift time would become.

The interaction of the modifier to the component of the sample does not need to be limited to one site of the component (molecule). For example as shown in FIG. 17, if the component 1704 has three different functional groups ($R_1$, $R_2$, & $R_3$), then three different modifiers ($M_1$, $M_2$, & $M_3$) 1705 can be added to the drift gas producing a drift media. The modifiers 1705 can have specific interactions with the functional groups ($R_1$, $R_2$, & $R_3$) producing bound component 1706. By three interacting modifiers, the additional drift time can be increased more than just having one modifier interact. We can tune the interaction of each modifiers interaction by selection of the modifier for the specific interaction. In addition, modifiers can interact with each other before or after interacting with the component to increase the drift time of the component. As shown in FIG. 17, component 1707 interacts with modifier $M_1$ of 1708 to form bonded component 1709 where $M_2$ is attached to $M_1$ and $M_3$ is attached to $M_2$.

In one embodiment of the present invention, an ion mobility based separation method can be used which comprises: ionizing components of a sample; separating at least one component of the sample in a drift media based on their measured ion mobility characteristics; and changing the measured ion mobility characteristics through an ion molecular interaction between the ionized components and the drift media, where the ion molecular interaction involves at least one matching property of the components and the drift media. The drift media can comprise, one or more of noble drift gas, interactive drift gas, and/or modifier in a known ratio that is in a range of zero to one hundred percent.

Chromatography separation methods are generally polarity driven. Meaning, compounds in a mixture with different polarities elute from the column at different retention times. The mixtures are separated utilizing a mobile phase and a stationary phase. The various forms of chromatography, gas (GC), liquid (LC), supercritical fluid (SFC), ion exchange, etc. differ by the physical state of the mobile phase (GC vs. LC) or by the mechanism of separation. The high pressure liquid chromatography (HPLC) method will be explained below, even though other chromatographic techniques can be utilized such as chiral chromatography, ion chromatography, GC and SFC.

Figure 2:
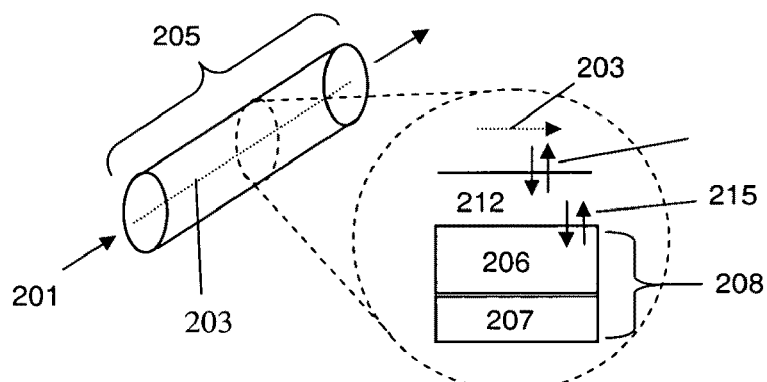
FIG. 2 shows the HPLC retention model.

HPLC is a versatile, proven chromatographic technique for high-resolution separation of molecules involving a dynamic adsorption process using a moderate to high-pressure flow for the mobile phase. The stationary phase is an adsorbent and the separation is based on repeated adsorption-desorption steps where surface interactions compete. Two modes are defined based on the relative polarity of the two phases: normal, where the stationary bed is strongly polar and the mobile phase is nonpolar, and reversed, where the inverse is true. In normal phase, polar molecules are retained longer than less polar molecules. The retention mechanism for HPLC uses dipole-dipole (polar) interactions in normal phase and hydrophobic (non-specific) interactions in reversed phase. Depending on the type of functional group exposed on the surface, the adsorbent could be normal phase (—OH, —$NH_2$) or reversed phase (C8, C18, Phenyl). The stationary phase can also be chemically modified to increase polar interactions in normal phase by chemically bonding organic ligands to significantly change the adsorption properties of the silica surface, where the ligand type determines the adsorbent retentive power and selectivity. The retention model shown in FIG. 2 assumes a small amount of sample 201 does not significantly disturb the mobile phase 203 equilibrium in the column 205. If the ligand 206 bound to the stationary phase (silica) 207 prefers polar interactions, then highly polar molecules in the sample are retained on the stationary phase 208 longer than the less polar molecules. For HPLC separation, the overall retention is composed of two concurrent processes. First, the molecule partitions 210 from the mobile phase into the adsorption layer 212. Second, the molecule competes for the polar interaction on the stationary phase. A molecule will adsorb 215 and be retained on the stationary phase only if the sample's interaction is stronger than the mobile phase's interaction; thus, the molecule's retention time corresponds to the strength of its interaction.

In chemistry, polarity refers to a separation of electric charge leading to a molecule having an electric dipole. Polar molecules can bond together due to dipole-dipole intermolecular forces between one molecule (or part of a large molecule) with asymmetrical charge distribution and another molecule also with asymmetrical charge distribution. Molecular polarity is dependent on the difference in electronegativity between atoms in a compound and the asymmetry of the compound's structure. When comparing a polar and non-polar molecule with similar molar masses, the polar molecule generally has a higher boiling point, because of the dipole-dipole interaction between their molecules. The molecules polarity underlies a number of physical properties including surface tension, solubility, and melting- and boiling-points. Many molecules have non-uniform distributions of positive and negative charges on the various atoms. Such is the case with ionic compounds like hydroxide ($OH^-$), where electron density is shared unequally between atoms. Therefore, the charge distribution will be different on each molecule. Sucrose, a sugar variety has many polar oxygen-hydrogen (OH) groups and are overall highly polar. For large molecules there maybe polar and non-polar regions. Surfactants are large molecules that have one end with polar groups attached and the other end with non-polar groups. While the molecules can be described as "polar covalent", "non-polar covalent", or "ionic", it must be noted that this is often a relative term, with one molecule simply being more polar or more non-polar than another.

Figure 3:
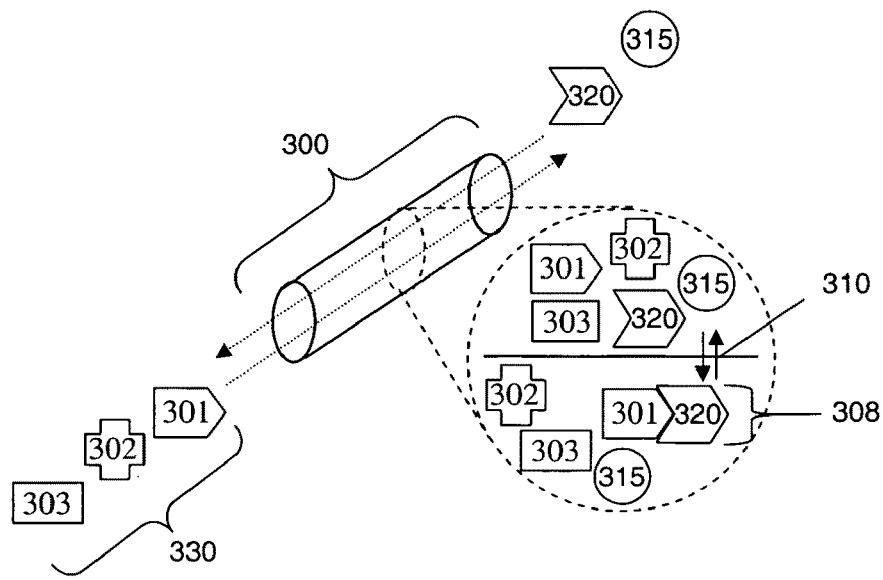
FIG. 3 shows the dynamic polar interaction in an IMS drift tube.
Figure 4:
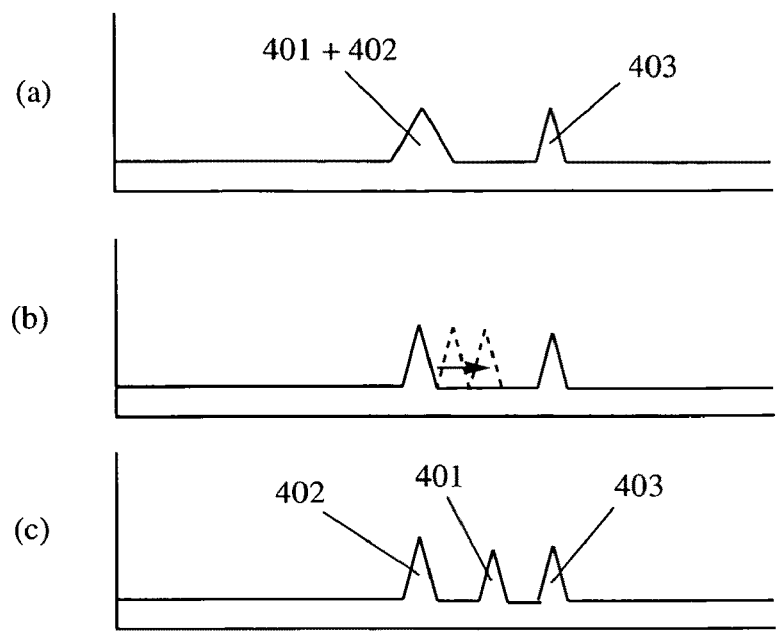
FIG. 4 shows the dynamic medium separation.
Figure 5:
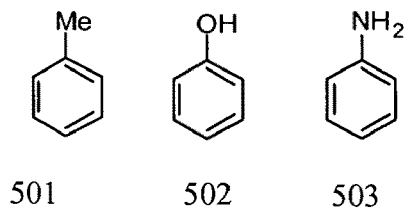
FIG. 5 shows three modifiers have very similar mass and size varying in polarity that are used to affect component separation.

In one embodiment of the present invention, the matching property of the components of the sample to be separated other than the ion mobility, i.e. reduced mass, collection cross section (size and/or shape) and type of charge state of the components to enhance separation and/or resolution of the sample is the components and drift media's overall polarity. Similar to HPLC principles, the IMS polarity driven separation technique uses a modifier or modifiers, which are added to the drift gas that selectively interact, to some degree, with one molecule of the sample over the others by the inherent polarity of the molecule. A modifier can thus be added to the drift gas that interacts strongest with the most polar ions in the drift tube for the longest period of time, while less polar ions would interact for shorter times, furnishing a polarity driven IMS separation. FIG. 3 shows an expanded section of the drift tube 300, where the most polar component ion 301 of the sample has a strong polarity-based interaction 308 with the modifier 320. The other components of the sample 302 and 303 are less polar molecules than component 301. In this non-limiting example, the modifier 320 is added with the drift gas 315 and travels down the drift tube 300 in the opposite direction as the sample component ions 330. The drift gas and modifiers can be added in various different axes compared to the sample traveling axis. For example, the drift gas and modifier can be added in a perpendicular direction such that the drift gas and modifier is added as a crossflow. During the time the ions are in the drift tube and/or reaction region, a dynamic polar interaction 310 ensues, slowing the travel of 301 through the constant electric field because component 301 is the most polar component and has the strongest interaction with the modifier 320. For example, given three different amino acids threonine, valine, and phenylalanine in a sample, a traditional IMS drift spectrum would only separate 1 of the 3 amino acids as simulated in FIG. 4 spectra (a). Phenylalanine 403 has the largest molecular weight (MW) of 165 amu and therefore has the longest drift time. Threonine 401 with a MW of 119 and valine 402 with a MW of 117 are not distinguishable from each other as the mass difference is only 2 amu. In order to separate threonine 401 and valine 402 from one another, a modifier can be added to the drift gas to move one of these two components to a longer drift time as shown in FIG. 4 spectra (b). Since threonine 401 is a more polar molecule than valine 402, a modifier that interacts with the most polar component is used. Consequently, the less polar valine 402 does not interact with the modifier like threonine 401 and travels faster through the drift region and/or reaction region of the IMS with a shorter drift time than valine 402. Therefore, valine 402 and threonine 401 are separated by targeting the polar properties inherent to each component of the sample and are shown in FIG. 4 spectra (c). The polarity-driven IMS separation mechanism derives from the intermolecular forces between the sample ions and the modifier. Unlike covalent and ionic bonding, these interactions are non-stable, momentary attractions that can arise from dipole-dipole interactions between molecules with permanent dipoles having an electrostatic interaction between the two point dipoles, through hydrogen bonding, clustering, or other interaction force. More electronegative atoms like nitrogen, oxygen, and halogens tend to have partial negative charges, while atoms like carbon and hydrogen tend to be more neutral or have partial positive charges. Hydrogen bonding is a special dipole-dipole interaction between two highly electronegative atoms with the hydrogen covalently bound to one molecule that acts as a hydrogen donor to the other molecule. The drift media consists of the drift gas and modifier, the drift gas can also be changed to enhance the separation along with the modifier. Choosing a less polar drift gas would enhance the interaction between the polar component and the polar modifier since the interaction would be magnified, analogous to changing the mobile phase in the normal phase HPLC where the solvents are mainly non-polar. The composition of the mobile phase is one of the variables influencing the separation as the sample competes with the mobile phase for positive surface interactions with the stationary phase. Modifiers used in the novel IMS separation can be added separately or together as a mixture. Modifiers with similar size and/or shape would be used in the IMS, so that the modifiers would cause similar ion mobility changes and the modifiers polarity interaction would be the driving factor in the separation of the molecules. Modifiers of similar size that have a broad spectrum of polarity (from low to high) would be used to effect molecule separation. Molecules with similar polarity tend to be attracted to each other; those with dissimilar polarity exhibit much weaker attraction, if any, and may even repel one another. The amount of these modifiers could be adjusted on-the-fly as a gradient. Modifier concentration could be increased or decreased to tune the polarity driven IMS separation; the gradient of modifiers can be controlled by introducing less polar modifier to more polar modifier, or more polar to less polar to the drift gas. FIG. 5 shows three modifiers varying in polarity that are used to affect component separation and have a very similar size. Modifier 501 is the least polar, modifier 502 is more polar, and modifier 503 is the most polar. Each modifier could be added separately or together as a mixture. The amount of the modifiers could be adjusted on-the-fly as a gradient. The method of adding these modifiers may be involve adding a certain amount of the modifiers forming constant concentration of modifier in the drift media; the ion mobility measurement is conducted under a constant modifier condition. Alternatively, modifier concentration could be increased or decreased while a sequence of ion mobility measurements is conducted; the gradient of modifiers can be controlled by introducing less polar modifier to more polar modifier, or more polar to less polar to the drift gas.

Given two components in a sample having the same ion mobility in a drift media, but different polarity, the polar component has a stronger interaction with the polar modifier when modifier is added into the drift media. Consequently, the less polar component travels faster through the drift region of the IMS, thus the two components can be separated. In an alternative embodiment, as the drift media consists of drift gas and modifier(s), the drift gas can also be changed to enhance the separation along with the modifier(s). For example, choosing a less polar drift gas would enhance the interaction between the polar component and the polar modifier since the interaction would be magnified.

Figure 6:
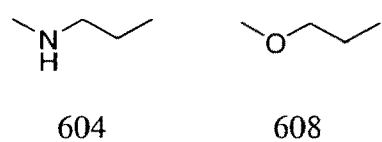
FIG. 6 shows two components of a sample that have very similar molecular weights but different overall polarity.

By using the principles of polarity discussed previously, a modifier can be chosen to distinguish two components of a sample that have very similar molecular weights and/or size and shape by targeting the additional property of the components (their polarity). For example, as shown in FIG. 6, N-methylpropylamine 604 ($C_4H_{11}N$) has a molecular weight of 73 and methyl propyl ether 608 ($C_4H_{10}O$) has a molecular weight of 74. Both of these molecules are very similar in size and shape and the bond connectivity is the same. However, each molecules overall polarity is different. Methyl propyl ether 608 is more polar than N-methylpropylamine 604. The presence of an oxygen is more polar than a nitrogen because oxygen is more electronegative than nitrogen. The greater the electronegativity difference between atoms in a bond, the more polar the bond.

Larger molecules may have a plurality of functional groups that can influence the molecules overall polarity. A molecule's structure, activity, and physicochemical characteristics are determined by the arrangement of its constituent atoms and the bonds between them. Within a molecule, a specific arrangement of certain atoms that is responsible for special properties and predictable chemical reactions is called a functional group. This structure often determines whether the molecule is polar or non-polar. Organic molecules are sorted into classes according to the principal functional group(s) each contains. Using a IMS separation technique based on polarity, the drift time of different kinds of molecules can be determined by the nature and location of these functional groups. In general, the ranking of functional groups are from most polar to least polar are: Amide>Acid>Alcohol>Ketone~Aldehyde>Amine>Ester> Ether>Alkane.

Figure 7:
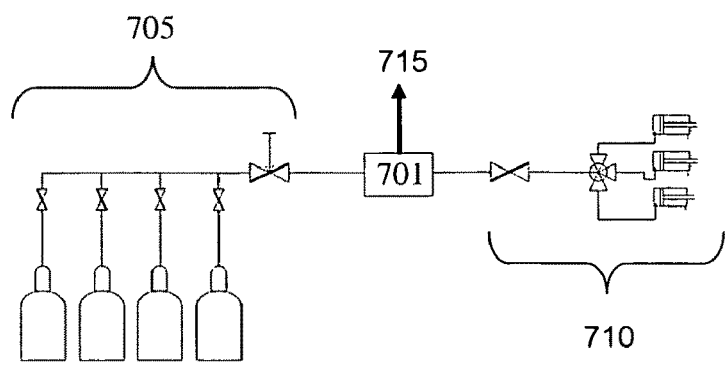
FIG. 7 shows the dynamic drift media generator that allows mixing different gases, as well as using a gas or gas mixture as a carrier to deliver known concentrations of premixed liquid modifiers as the drift media.

Another embodiment of the invention is to control the number and/or concentrations of the modifiers and drift gases that the components of the sample interact with in the IMS. A dynamic drift media generation and control mixer is used to switch between different drift media in seconds as shown in FIG. 7. Typically, samples are continuously infused into the IMS via an ESI source so that a series of ion mobility spectra could be obtained using one drift media composition and then switched to the next. The dynamic drift media generator 701 rapidly mixes and purges different drift media in an automated fashion. FIG. 7 shows a proposed dynamic drift media generator that allows mixing different gases 705, as well as using a gas or gas mixture as a carrier to deliver known concentrations of premixed modifiers 710 as the drift media to the drift tube 715. The system involves precise temperature controls to evaporate liquid chemical modifiers and preheat the drift gas to the temperature required by the IMS.

Figure 8:
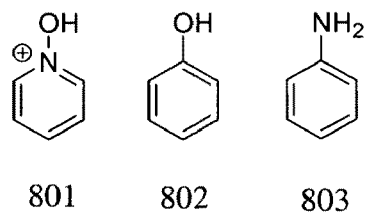
FIG. 8 shows three modifiers have very similar mass and size varying in $pK_a$ that are used to affect component separation.

In another embodiment of the present invention, the matching property of the components of the sample to be separated is the components and drift media's inherent pH. In this non-limiting example, a modifier would be added to the drift gas that targets the matching properties of the components, i.e. acidity or basicity of the components. Modifiers having similar mass and size would be added to the drift gas, so that the conventional collisions of the components with the different modifiers used would not affect a mobility difference. FIG. 8 shows three modifiers varying in $pK_a$ that are used to affect component separation and have very similar mass and size. Modifier 801 has a $pK_a$ of 0.7, modifier 802 has a $pK_a$ of 10, and modifier 803 has a $pK_a$ of 41. The modifiers could be added separately, as a mixture, or as a gradient (lower $pK_a$ to higher $pK_a$ or higher $pK_a$ to lower $pK_a$) to the drift gas. The matching property can be the same or opposite. For example, acidic components are preferred to interact with a basic drift media, and basic components are preferred to interact with an acidic drift media.

The acidity of each component of the sample can be significantly or slightly different and can be targeted by adding at least one modifier to the drift gas. Bases can be thought of as the chemical opposite of acids, therefore basicity is understood to be the opposite of acidity. For acidity, as the electron density on hydrogen decreases it is more easily abstracted, in other words, it is more acidic. The electronegative element need not be directly bonded to the acidic hydrogen to increase its acidity. An electronegative atom can pull electron density out of an acidic bond through the inductive effect. The electron-withdrawing ability diminishes quickly as the electronegative atom moves away from the acidic bond.

Figure 9:
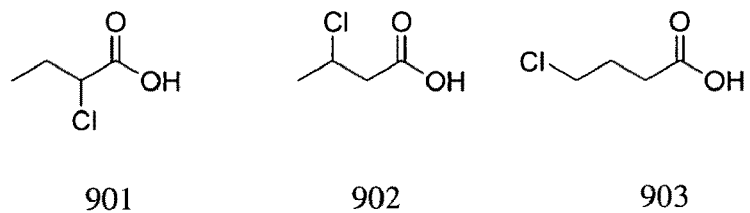
FIG. 9 shows three components of a sample that are different isomeric forms that have the same molecular weight but different $pK_a$ values.

A non-limiting example is shown in FIG. 9 where three components of the sample are different isomeric forms; 2-chlorobutanoic acid 901, 3-chlorobutanoic acid 902, and 4-chlorobutanoic acid 903. The molecular weight of each molecule is the same (MW=124), but the acidity ($pK_a$) is different for each molecule. Stronger acids have a smaller $pK_a$ than weaker acids. As the chlorine atom moves further away from the acidic O—H bond, its electron withdrawing effect diminishes. The $pK_a$'s for these three compounds are: 2-chlorobutanoic acid 901 $pK_a$=2.86, 3-chlorobutanoic acid 902 $pK_a$=4.0, and 4-chlorobutanoic acid 903 $pK_a$=4.5. Therefore, a modifier that has a high pKa will interact the strongest with the lowest $pK_a$ of the component in the sample, because the modifier is the conjugate base. Reactions of acids are often generalized in the form HA $H^+ + A^-$, where HA represents the acid and $A^-$ is the conjugate base. Acid-base conjugate pairs differ by one proton, and can be interconverted by the addition or removal of a proton (protonation and deprotonation, respectively). Note that the acid can be the charged species and the conjugate base can be neutral in which case the generalized reaction scheme could be written as $HA^+ H^+ + A$. For example, if we were running a gradient of modifiers such as the three in FIG. 8 to separate the three components of a sample shown in FIG. 9, then modifier 803 would interact the strongest with component 901, compared with components 902 and 903. The overall pH (acidity or basicity) of the components is the additional property that is targeted by the modifier(s) to elicit the desired separation of the components in the sample.

In another embodiment of the present invention, the matching property of the components of the sample to be separated is the components and drift media's surface tension. In this non-limiting example, a micelle could be added to the drift gas that targets the interfacial tension of the component. A molecule in contact with a neighbor is in a lower state of energy than if it wasn't in contact with a neighbor. The interior molecules all have as many neighbors as they can possibly have. But the boundary molecules have fewer neighbors than interior molecules and are therefore in a higher state of energy. For the component to minimize its energy state, it must minimize its number of boundary molecules and must therefore minimize its surface area. In addition, the modifier could be a surfactant, phospholipid, or a colloid. This interaction may become significant while conducting ion mobility measurement in liquid phase or high pressure conditions (e.g. several atmospheric pressures)

Yet another embodiment of the present invention, the matching property of the components of the sample to be separated is the components and drift media's inherent charge strength (that could be ether positive ions or negative ions). This would be similar to the way ion exchange chromatography separates molecules based on differences between the overall charge of proteins. The novel method involves a drift media, in particular adding at least one modifier to the drift gas of an ion mobility spectrometer (IMS) that interacts to a greater degree with the component of the sample that has the greatest charge strength. A specific aspect of this embodiment is using a cation/anion-π interaction method to target the components of the sample differences in charge strength.

Figure 10:
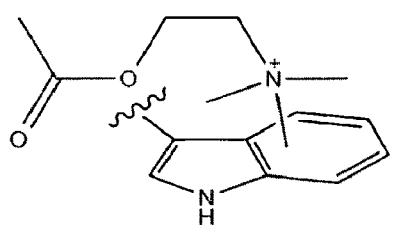
FIG. 10 shows an example of a cation-π interaction.

The cation-π interaction is a noncovalent molecular interaction between the face of an electron-rich π system (e.g. benzene, ethylene) with an adjacent cation (e.g. $Li^+$, $Na^+$). This interaction is an example of noncovalent bonding between a monopole (cation) and a quadrupole (π system). Cation-π interaction energies are of the same order of magnitude as hydrogen bonds or salt bridges and play an important role in molecular recognition. The cation-π interaction is comparable in strength to hydrogen bonding and can, in some cases, be a decisive intermolecular force. Several criteria influence the strength of the bonding: the nature of the cation, the substitutents on the π system, as well as the solvent when being used in HPLC applications. The cation-π interaction is not just for metals. Studies in the mid 1980's by Meot-Ner demonstrate the more complex organic cations are also good binders in the gas phase. The cation-π interaction has been used in drug design, structural biology, conformational analysis and asymmetric catalysis. Amino acid side chains of tryptophan and tyrosine or the DNA bases are capable of binding to cationic species (not only metal ions, but also charged amino acid side chains. Therefore, cation-π interactions can play an important role in stabilizing the three dimensional structure of a protein. An alternative role of the cation-π interaction is shown in FIG. 10, where the nicotinc acetylcholine receptor binds its endogenous ligand, acetylcholine (a positively charged molecule), via a cation-π interaction to the quaternary ammonium.

Anion-π interaction is opposite to cation-π interaction, although the underlying principles are identical. Significantly less examples are known to date. In order to attract a negative charge, the charge distribution of the π system has to be reversed. This is achieved by placing several strong electron withdrawing substituents along the π system (e.g. hexafluorobenzene).

One embodiment of the invention is to add at least one modifier to the drift gas to create a cation-π interaction that differentiates between the positive ion components of the sample. The modifier retards the travel down the drift tube via the cation-π interaction of the most strongly positive ion component. The strength of the ions cationic charge can be different for different molecules for a number of reasons. The atoms and their position that make-up the molecule plays an important role toward contributing to the cationic strength. Therefore each component of the sample has a different overall positive charge strength.

Figure 11:
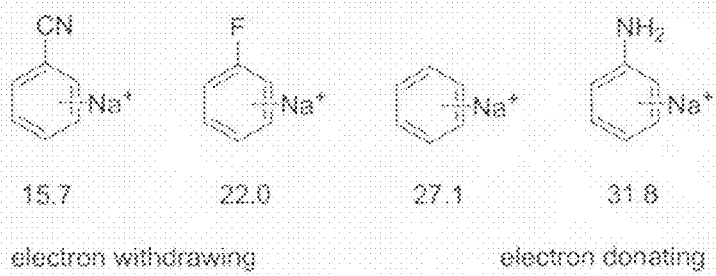
FIG. 11 shows the effect on the π system by adding various substituents.

The electronic properties of the substituents on the π system also have an influence on the strength of the attraction. Therefore in this case, the modifiers can be selected or tuned by changing functional groups on the modifier to elicit a desired interaction strength with the component of the sample of interest. Electron withdrawing groups (e.g. Cyano —CN) decrease the amount of negative charge in the π system and thus weaken the interaction. On the contrary, electron donating substituents (e.g. amino —$NH_2$) increase the charge separation of the quadrupole and strengthen the cation-π binding. This relationship is illustrated quantitatively in FIG. 11 for several substituents.

Figure 12:
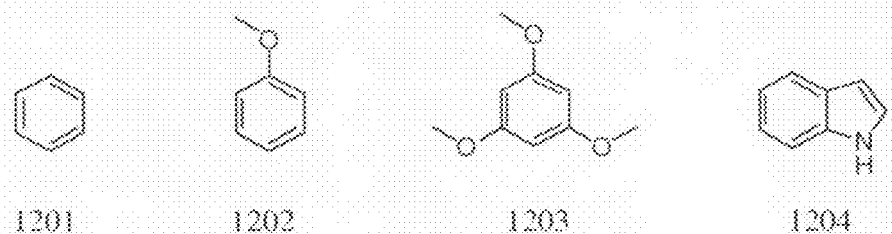
FIG. 12 shows some selected modifiers used for the cation-π interaction.
Figure 13:
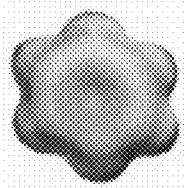
FIG. 13 shows the electrostatic surface for the benzene ring.
Figure 14:
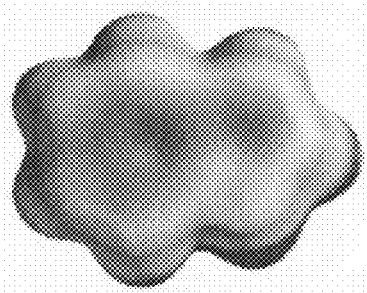
FIG. 14 shows the electrostatic surface for the indole molecule.

Some selected modifiers, benzene 1201, anisole 1202, trimethoxybenzene 1203, and indole 1204 that could be used for the cation-π interaction are shown in FIG. 12. These are only some representative examples and are non-limiting. Anisole 1202, trimethoxybenzene 1203, and indole 1204 all have electron donating substituents on the π system. The electrostatic surface for the benzene ring is shown in FIG. 13. The theoretical value for gas phase binding of benzene with Na+ in kcal/mol is 27.1. By adding a electron donating substituent on the it system, such as the indole molecule, the value increases to 32.6 as shown in FIG. 14.

In a non-limiting example, given two components in a sample to be separated with similar masses, one has a electron withdrawing group (EWG) on the molecule EWG-$NH_4$+ and the other component has a electron donating group (EDG) on the molecule EDG-$NH_4$+. Since the masses are identical, but the overall positive ion charges are different strengths, a modifier is added to target this additional property of the components of the sample. Indole is selected and added to the drift gas as a modifier to induce a cation-π interaction. The EWG-$NH_4$+ molecule's travel is retarded more than the EDG-$NH_4$+ molecule because indole interacts more strongly with the EWG-$NH_4$+ molecule. The EWG-$NH_4$+ molecule's cationic charge is greater due to the electron withdrawing group adjacent to the $NH_4$+. Targeting this additional property of the components enhances the mobility based separation.

Yet another embodiment of the invention is to add at least one modifier to the drift gas to create a anion-π interaction that differentiates between the negative ions. The modifier retards the travel down the drift tube via the anion-π interaction of the most strongly negative ions. The strength of the ions anionic charge can be different for different molecules for a number of reasons. The atoms and their position that make-up the molecule plays an important role toward contributing to the anionic strength.

Figure 15:
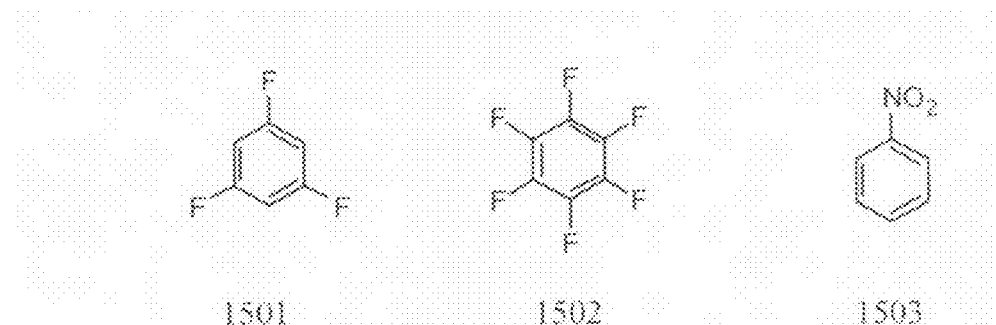
FIG. 15 shows some selected modifiers used for the anion-π interaction.
Figure 16:
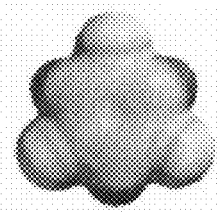
FIG. 16 shows the electrostatic surface for the trifluorobenzene molecule.

Some selected modifiers, trifluorobenzene 1501, hexafluorobenzene 1502, and nitrobenzene 1503 are shown in FIG. 15 that could be used for the anion-π interaction. These are only some representative examples and are non-limiting. By adding electron withdrawing groups, trifluorobenzene has a value of 12.4 compared to benzene as shown in FIG. 16.

Another embodiment of this invention is to add drift media that interacts selectively, to some degree, with one component over the other(s) by a matching property of the component, i.e. affinity. Affinity is the tendency of a molecule to associate with another. Some examples of affinity can be but not limited to: an interaction force, the molecular surface (shape or volume through atom pair matching function and surface potential through charge matching function), and binding to a biological target (receptor, enzyme, transport system, etc.). In this non-limiting example, the drift media can have one or more molecules associated with each other. For example, if two drift media molecules A and B are associated together, a third molecule C (a component of the sample) can displace the weaker molecule (in this case B) to form a stronger association A and C because the affinity of A and C is greater than the affinity A and B. Therefore in an IMS based separation, a component of the sample with a high affinity for the drift media will compete effectively for binding sites, and thus displace molecules with lesser affinities in the drift media. In another aspect, the molecule A and B may recombine after departure of the component C. This affinity with the drift media will slow the drift time for the component that has the stronger affinity compared to the component that has a weaker affinity, thereby separating these components via their affinities for the drift media. For two components to travel at different speeds, and thereby be separated/resolved, there must be substantial differences in some interaction between the components of the sample and the drift media. The drift media of the IMS are adjusted to maximize the effect of this difference.

Another embodiment of this invention is to add drift media that interacts selectively, to some degree, with one component over the other(s) by another matching property of the component, i.e. size-exclusion properties. The components of a sample can be separated based on their hydrodynamic volume by adding a drift media that momentarily traps (interacts) a component that has a particular size and/or shape. In host-guest chemistry an inclusion compound is a complex in which one chemical compound (the "host") forms a cavity in which molecules of a second "guest" compound are located. In this non-limiting example, the drift media is added that will momentarily trap small components of the sample over large components. The drift media molecules have a cavity (hole) that the small components can fit into, but the large components cannot. Large components cannot enter the drift media molecules and are excluded. Since they don't enter the drift molecules they just collide with them. Small components can enter the drift media molecules and their travel is retarded compared with just colliding with them and are detected later. In one embodiment of this invention, fine (micron and/or nano) particles that can provide the size exclusion properties can be mixed into the drift media entrain with drift flow homogenously or heterogeneously to achieve the intended separation. Note that these particles are made electrophobic (with low charge affinity) to ensure they would not remove charges from the sample components.

Another embodiment of this invention is to add drift media that interacts selectively, to some degree, with one component over the other(s) by another matching property of the component, i.e. size-exclusion properties. The components of a sample can be separated based on their hydrodynamic volume by adding a drift media that momentarily traps (interacts) a component that has a particular size and/or shape. In host-guest chemistry an inclusion compound is a complex in which one chemical compound (the "host") forms a cavity in which molecules of a second "guest" compound are located. In this non-limiting example, the drift media is added that will momentarily trap small components of the sample over large components. The drift media molecules have a cavity (hole) that the small components can fit into, but the large components cannot. Large components cannot enter the drift media molecules and are excluded. Since they don't enter the drift molecules they just collide with them. Small components can enter the drift media molecules and their travel is retarded compared with just colliding with them and are detected later. In one embodiment of this invention, nano-particles and/or macro molecules that can provide the size exclusion properties can be mixed into the drift media entrain with drift flow homogenously or heterogeneously to achieve the intended separation. Note that these particles are made electrophobic (with low charge affinity) to ensure they would not remove charges from the sample components.

In additional to choose drift media that achieve the maximum separation of targeted sample components, such components can be a pair of enantiomers or chemical/biological molecules that overlaps in a conventional ion mobility based spectrometer where on pure noble gas drift media is used, the present invention also describes methods and apparatus to tune the performance of an ion mobility based spectrometer by altering the degree of interaction between the ionized sample components and drift media. The tuning method involves adding energy to the components of the sample to be separated and/or the neutral molecules in the drift media that may interact with sample components. The degree of interaction between the ionized sample components and neutral molecules in drift media is in a range from no interaction (the ions and neutral molecules undergo elastic collision) to compete interaction (the ions and neutral molecules form a permanent cluster or product ion); in between, ions and neutrals molecules may interact based on their matching properties causing measured ion mobility characteristic (e.g. drift time) change; or they may form transient clusters that have a life time that is significantly shorter that the analysis time in the spectrometer. The tunable ion mobility based spectrometer and methods described in this invention is intended to optimize the degree of interaction that may include but not limited to, preventing ions and neutral molecules from forming a cluster or clusters, selectively preventing certain ions and/or neutral molecules from forming cluster(s), altering the life time of the cluster(s), elevating the ions and/or neutral molecules to a energy level to enable the interaction, tuning to a given energy level where the sample component and modifier have optimal interaction resulting maximum separation of sample components.

In one embodiment, the method of tuning the ion energy with an energy source in-conjunction with adding a chemical modifier to the drift media may enhance and/or control the degree of the interaction of the drift media (including chemical modifiers) with the ions thereby improving the overall separation of the sample ions.

Figure 18:
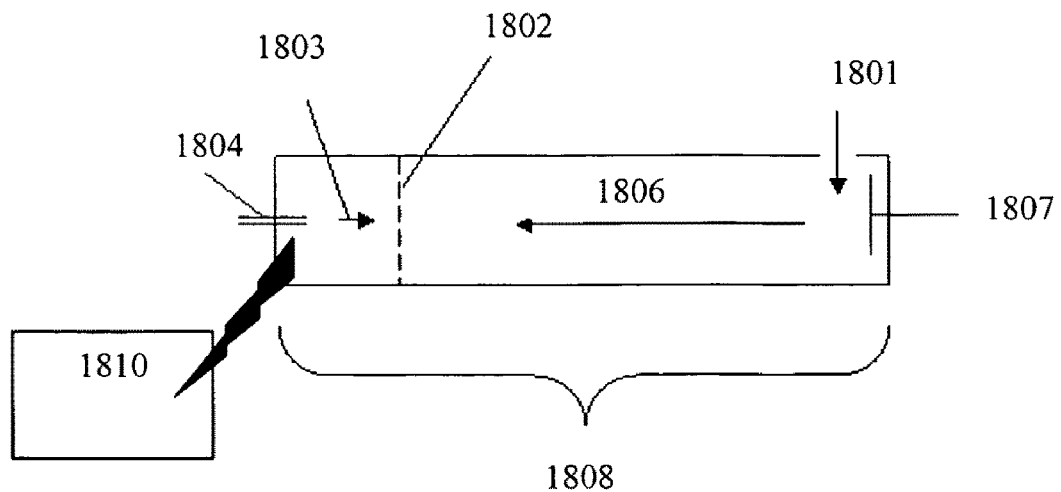
FIG. 18 shows adding energy to either the components or the drift media.

The present invention uses an energy source to supply energy to ions or neutral molecules in an ion mobility based spectrometer as a means to optimize the interaction between ions and neutral molecules to achieve optimal separation in these devices. Not only the neutral gas (drift gas), but at least one chemical modifier is also supplied to the spectrometer. The chemical modifier undergoes a gas phase interaction with the ions to be separated. The ion energy is tuned to achieve optimal separation for the given ions in the media (including both drift gas and chemical modifier). The ion energy level could be scanned from low to high during the separation process. For example, acquiring one ion mobility spectrum under one energy level, and then acquiring another ion mobility spectrum at a different energy level; the process could be repeated until maximum ion mobility based performance can be achieved. The energy source can supply energy to the ions in any region of the spectrometer, the ionization, reaction, and/or drift. As a non-limiting example, FIG. 18, shows the drift media 1801 is introduced into the IMS in drift region. In a time of flight IMS, the drift tube is separated ionization/reaction region and drift region by an ion gate 1802. Sample components are ionized before the ion gate 1802 and then guided into the drift region under influence of electric field. The ion trajectory 1803 and the drift media flow 1806 in opposite directions. With an energy source 1810, sample components and/or drift media in the drift tube 1808 are tuned at an energy level that is suitable for the ion mobility based separation. The separated sample components are collected or detected at the end of drift tube on collector 1807.

Figure 19:
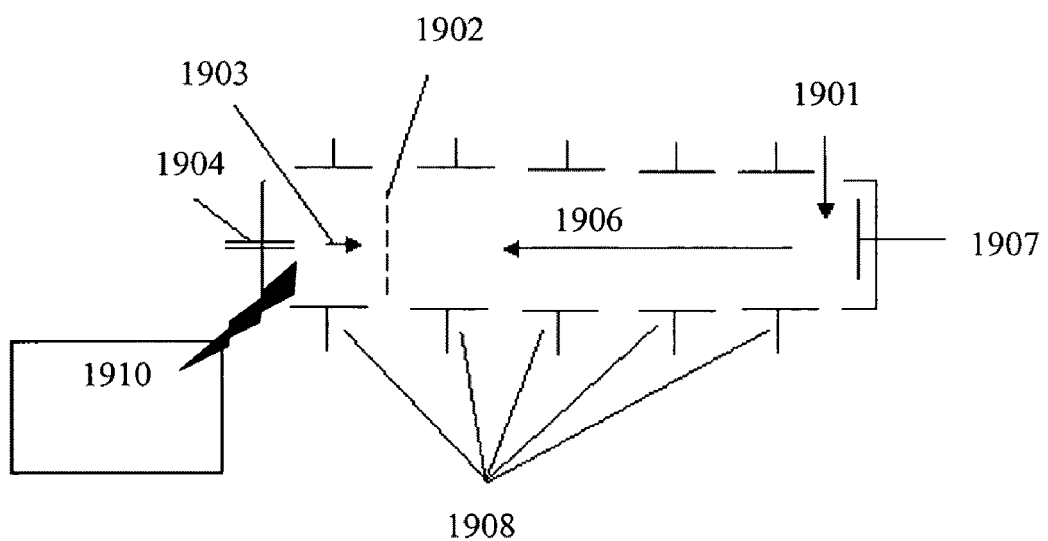
FIG. 19 shows adding an RF energy and an additional energy source.

The ions energy in the ion mobility based spectrometer can be tuned by supplying an RF electric field to the ions as described in patent application Ser. No. 12/026,192. By adjusting the frequency, amplitude and/or other parameter of the RF waveform, the ion energy is tuned while being separated either based on their static ion mobility in a time of flight ion mobility spectrometer or ion mobility variation in a field asymmetric ion mobility spectrometer. As a non-limiting example, FIG. 19, shows a TOF-IMS using electrodes that are biased with both DC and RF fields. Similarly, the drift media 1901 is introduced into the IMS in drift region. In the time of flight IMS, the drift tube is separated into ionization/reaction region and drift region by an ion gate 1902. Sample components are ionized before the ion gate 1902 and then guided into the drift region under influence of electric fields. In this case, a RF electric field is added to the drift tube (ionization and/or drift region) through electrodes 1908 to maintain the ions at a given energy level (the apparatus and methods of adding RF electric field to an IMS is described in U.S. patent application Ser. No. 12/026,192). The ions travel through the drift media flow 1906 with a direction of 1903. In one embodiment, an energy source 1910 can be used with the RF electric field either simultaneously or as an alternative energy source to achieve the performance goals. When used simultaneously, the additional energy source 1910 and RF electric field may be used to energize difference sample components, neutral molecules that are associated with the sample components, and/or drift media. As a non-limiting example, the RF electric field can be used to keep the sample components from clustering with the surrounding neutral molecules (such as water), and the additional energy source 1910 is tuned to achieve separation based on the component-drift media interaction. Alternatively, the additional energy source 1910 using a laser beam that is guided to inside a drift tube with an bandwidth that selectively heat up the water molecule, thus prevent them from clustering, and the RF electric field maintains the sample component ions at a energy level that is suitable for the component-drift media interaction achieving the ion mobility based separation. The separated sample components are collected or detected at the end of drift tube on collector 1907.

In a variety of embodiments, an ion mobility based spectrometer can be equipped with an energy source. The ion mobility based spectrometer comprises a drift media wherein at least one component of the sample is separated from the other components based on their measured ion mobility characteristics; an energy source that provides energy in addition to the thermal energy at a given operational temperature to the ionized sample components, neutral molecules associated with the sample components and/or the drift media. The additional energy can influence the separation in the ion mobility based spectrometer by altering the degree of ion molecular interaction between sample components and drift media.

A ion mobility based spectrometer, comprising: a drift media wherein at least one component of the sample separated based on their ion mobility characteristics; an energy source that providing energy in addition to the thermal energy at a given temperature to the sample and/or the drift media influencing the separation of the components in the sample; and the energy level can be tuned to alter the degree of interaction between sample components and drift media for the separation of the components. The drift media comprises; one or more of noble drift gas, interactive drift gas, and/or modifier in a known ratio that is in a range of zero to one hundred percent. The energy source generates a range of electromagnetic energy, in particular in the visible, infrared, microwave radio range. The energy is from a source comprising a laser and/or radio frequency electric field. The energy is also used to prevent neutral molecules from clustering with sample components prior to and/or during the separation in the drift media.

The ion mobility based spectrometer wherein the energy is generated using means of a range of electromagnetic energy, in particular in the visible, infrared, microwave radio range. As an non-limiting example, the energy may from a source comprising a laser and/or radio frequency electric field. The added energy to the sample components and/or drift media can also be used to prevent neutral molecules from forming clusters with the sample components prior to and/or during the separation in the spectrometer. The energy level for declustering and optimal separation may not necessary to be the same level. If required, the energy source may provide several different level of energy, e.g. the energy source may use one or more laser sources to provide photo energy at different wavelengths. Alternatively, the different energy sources can be used for same spectrometer simultaneously, e.g. a RF electric field and laser source are applied to the same spectrometer. In one embodiment, the additional energy is used to first remove the neutral molecules [pre-existing cluster(s)] from ionized sample component cluster(s) (preferably prior to enter the drift region of a ion mobility base spectrometer), subsequentially allowing the sample component in their free form to interact with drift media at a selected energy level in the drift region while maintaining a declusered component.

A ion mobility based separation method, comprising separating at least one component of the sample in a drift media while providing energy in addition to the thermal energy at a given temperature to the components, neutral molecules associate the components and/or the drift media to influence the separation of the components in the sample; the method also involved tuning the energy level to alter the degree of component-drift media interaction to optimize the separation of the components. The ion mobility based separation method may use the drift media comprises, one or more of noble drift gas, interactive drift gas, and/or modifier in a known ratio that is in a range of zero to one hundred percent. Wherein, the noble gas is commonly used in conversional ion mobility spectrometry device, such as, nitrogen, helium, air, etc.; interactive drift gas in this invention generally means molecules that are in gas phase under ambient conditions and are somewhat reactive, for example but not limited to, $CO_2$, $N_xO_x$, $SO_x$, $CF_4$, etc. The interactive gases can undergo a gas phase ion molecular interaction with ions in the ion mobility based spectrometer when used as drift media either in pure and/or mixed form. When mixed with other gases, the interactive gases can function as modifier of the drift gas (media). In one aspect, a modifier (or chemical modifier) means mixing one or more chemical (in gas, liquid, or solid form under ambient conditions) into the drift media (commonly a noble or interactive gas). The modifiers are generally in the same phase as rest of the drift media, e.g. a drift gas modifier is in gas phase under the operating condition of the ion mobility based spectrometer; if the drift media is in liquid phase, the modifier is also in liquid phase. By altering the drift media properties using a modifier, the sample components may undergo selective or non-selective interaction with the drift media. When operating an ion mobility based separation method the drift media may comprise noble gas, interactive gas, and/or chemical modifier in a ratio of zero to one hundred percent range.

What is claimed is:

1. An ion mobility based separation method, comprising:
   a. ionizing components of a sample;
   b. separating at least one component of the sample in a drift media based on their measured ion mobility characteristics; and
   c. changing the measured ion mobility characteristics through an ion molecular interaction between the ionized components and the drift media, where the ion molecular interaction involves at least one matching property of the components and the drift media in addition to their intrinsic ion mobility or ion immobility differences in the given drift media.

2. The ion mobility based separation method of claim 1, wherein the drift media comprises, one or more of noble drift gas, interactive drift gas, and/or modifier in a known ratio that is in a range of zero to one hundred percent.

3. The ion mobility based separation method of claim 1, wherein the matching property is the polarity of components and drift media.

4. The ion mobility based separation method of claim 1, wherein the matching property is the inherent pH of components and drift media.

5. The ion mobility based separation method of claim 1, wherein the matching property is the acidity of the components and drift media.

6. The ion mobility based separation method of claim 5, wherein the acidic components are preferred to interact with a basic drift media.

7. The ion mobility based separation method of claim 1, wherein the matching property is the basicity of the components and drift media.

8. The ion mobility based separation method of claim 7, wherein the basic components are preferred to interact with an acidic drift media.

9. The ion mobility based separation method of claim 1, wherein the matching property is the surface tension of components and drift media, particularly; surface tension of components is based on interfacial tension.

10. The ion mobility based separation method of claim 1, wherein the matching property is the inherent charge strength of the components and drift media.

11. The ion mobility based separation method of claim 10, wherein the inherent charge strength of the components and drift media through a cation-$\pi$ interaction.

12. The ion mobility based separation method of claim 10, wherein the inherent charge strength of the components and drift media through an anion-$\pi$ interaction.

13. The ion mobility based separation method of claim 1, wherein the matching property is the size exclusion of components and drift media.

14. The ion mobility based separation method of claim 1, wherein the matching property is the affinity components and drift media.

15. The ion mobility based separation method of claim 1, wherein the matching property is hydrophobic and/or hydrophilic properties.

16. The ion mobility based separation method of claim 1, wherein the interaction may involve the component interacting with one or more modifiers in the drift media.

17. The ion mobility based separation method of claim 16, wherein one of the modifiers interacts with one or more other modifiers in the drift media.

18. A ion mobility based separation method, comprising:
  a. separating at least one component of the sample in a drift media based on their measured ion mobility characteristics;
  b. providing energy in addition to the thermal energy at a given temperature to either the components or the drift media influencing the separation of the components in the sample; and
  c. tuning the energy level to alter the degree of separation of the components.

19. The ion mobility based separation method of claim 18, wherein the drift media comprises, one or more of noble drift gas, interactive drift gas, and/or modifier in a known ratio that is in a range of zero to one hundred percent.

20. The ion mobility based separation method of claim 18, wherein the energy is generated using means of a range of electromagnetic energy, in particular in the visible, infrared, microwave radio range.

21. The ion mobility based separation method of claim 18, wherein the energy is from a source comprising a laser and/or radio frequency electric field.

22. The ion mobility based separation method of claim 18, further comprises using the energy to prevent neutral molecules from clustering with sample components prior to and/or during the separation in the drift media.

23. A ion mobility based spectrometer, comprising:
  a. a drift media wherein at least one component of the sample is separated based on their ion mobility characteristics;
  b. one or more energy sources that provide energy in addition to the thermal energy at a given temperature to the sample and/or the drift media influencing the separation of the components in the sample; and
  c. the energy level can be tuned to alter the degree of interaction between sample components and drift media for the separation of the components.

24. The ion mobility based spectrometer of claim 23, wherein the drift media comprises; one or more of noble drift gas, interactive drift gas, and/or modifier in a known ratio that is in a range of zero to one hundred percent.

25. The ion mobility based spectrometer of claim 23, wherein the energy source generates a range of electromagnetic energy, in particular in the visible, infrared, microwave radio range.

26. The ion mobility based spectrometer of claim 23, wherein the energy is from a source comprising a laser and/or radio frequency electric field.

27. The ion mobility based spectrometer of claim 23, further comprises using the energy to prevent neutral molecules from clustering with sample components prior to and/or during the separation in the drift media.

* * * * *